United States Patent [19]

Mueller

[11] 4,133,820
[45] Jan. 9, 1979

[54] PERFLUOROALKYL MONOESTERS OF ANHYDRIDE 2,3,4,5-TETRAHYDROFURANTETRACARBOXYLIC ACID

[75] Inventor: Karl F. Mueller, New York, N.Y.

[73] Assignee: Ciba-Geigy Corporation, Ardsley, N.Y.

[21] Appl. No.: 828,460

[22] Filed: Aug. 29, 1977

Related U.S. Application Data

[62] Division of Ser. No. 646,689, Jan. 5, 1976, Pat. No. 4,058,537.

[51] Int. Cl.$^2$ ............................................. C07D 493/04
[52] U.S. Cl. ................................................ 260/346.74
[58] Field of Search ................................... 260/346.74

[56] References Cited

U.S. PATENT DOCUMENTS

| | | | |
|---|---|---|---|
| 3,182,073 | 5/1965 | Lonerini | 260/346.74 X |
| 3,711,514 | 1/1973 | Quick | 260/346.3 |

*Primary Examiner*—Richard L. Raymond
*Attorney, Agent, or Firm*—Luther A. R. Hall

[57] ABSTRACT

This invention describes new perfluoroalkyl substituted esters, diesters and polyesters which contain at least one cyclic 5-membered anhydride group or two carboxy groups, as well as half amides and half esters thereof; their synthesis and their use as surface-active reactants in polycondensate resin systems.

The anhydrides are synthesized by reaction of perfluoroalkyl substituted alcohols or diols with dianhydrides or an anhydrides-acid chloride and have the general structure

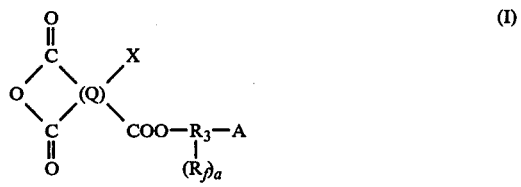

(I)

wherein: Q is the tetra-radical rest of a tri- or tetracarboxylic acid, which contains at least one 1,2-dicarboxy grouping,
X is hydrogen or COOH,
$R_f$ is perfluoroalkyl or perfluoroalkoxyperfluoroalkyl group of 4 to 18 carbon atoms,
a is 1 or 2,
A is hydrogen or

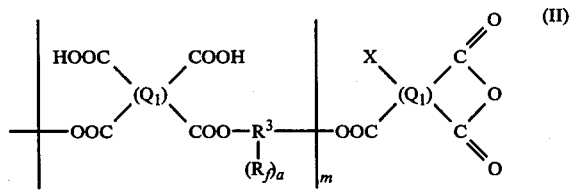

(II)

wherein: m is an integer from 0 to 5, and
$R^3$ is the residue of a $R_f$ substituted alcohol or diol.

7 Claims, No Drawings

PERFLUOROALKYL MONOESTERS OF ANHYDRIDE 2,3,4,5-TETRAHYDROFURANTETRACARBOXYLIC ACID

The present application is a divisional of application, Ser. No. 646,689, filed Jan. 5, 1976, now U.S. Pat. No. 4,058,537, issued Nov. 15, 1977.

The present invention pertains to perfluoroalkyl substituted anhydrides of the general formula

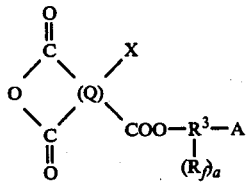

where Q is derived from 2,3,4,5-tetrahydrofurantetracarboxylic acid, which are useful in making surface active reactants, for which the essential material constituting a disclosure thereof is incorporated by reference from Ser. No. 646,689, filed Jan. 5, 1976, now U.S. Pat. No. 4,058,537.

What is claimed is:
1. A compound of formula I

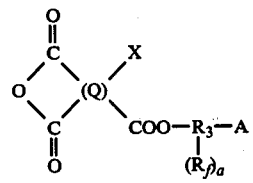

wherein
Q is the tetraradical rest of 2,3,4,5-tetrahydrofurantetracarboxylic acid;
X is carboxy;
$R_f$ is perfluoroalkyl of 6 to 18 carbon atoms;
a is 1 or 2;
A is hydrogen or group II;

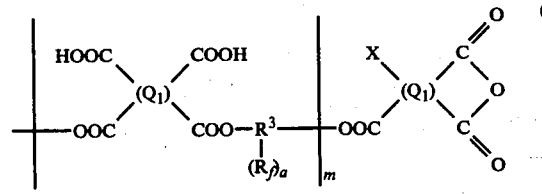

m is an integer from 0 to 2;
$Q_1$ is the same as Q, and
$R^3$ is the residue of an $R_f$-substituted aliphatic alcohol or diol of the structure

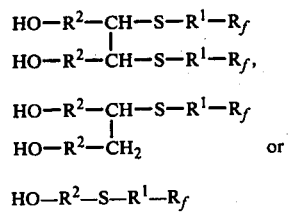

where $R^1$ is a branched or straight chain alkylene of 1 to 12 carbon atoms, alkylenethioalkylene of 4 to 12 carbon atoms, alkyleneoxyalkylene elen of 4 to 12 carbon atoms or alkyleneiminoalkylene of 4 to 12 carbon atoms where the nitrogen atom contains as the third substituent hydrogen or alkyl of 1 to 6 carbon atoms; and
$R^2$ is straight or branched chain alkylene of 1 to 12 carbon atoms or an alkylenepolyoxyalkylene of the formula $C_nH_{2n}(OC_kH_{2k})_r$ where n is 1 to 12, k is 2 to 6 and r is 1 to 40.

2. A compound according to claim 1 of formula I wherein Q is the tetraradical rest of 2,3,4,5-tetrahydrofurantetracarboxylic acid; X is carboxy; $R_f$ is perfluoroalkyl of 6 to 18 carbon atoms; a is 1 or 2; A is group II

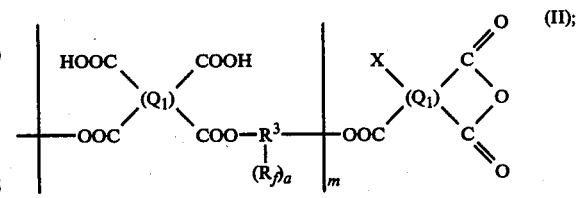

m is 0; $Q_1$ is the same as Q and
$R^3$ is the residue of an $R_f$-substituted aliphatic alcohol or diol of the structure

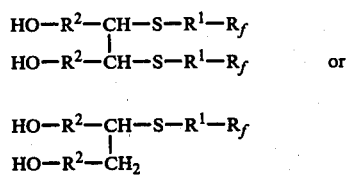

where $R^1$ is a branched or straight chain alkylene of 1 to 4 carbon atoms; and
$R^2$ is a branched or straight chain alkylene of 1 to 4 carbon atoms or alkylenepolyoxyalkylene of the formula $C_nH_{2n}(OC_kH_{2k})_r$ where n is 1 to 4, k is 2 to 4 and r is 1 to 20.

3. A compound according to claim 2 wherein $R^1$ is ethylene, and $R^2$ is methylene or methylenepolyoxyalkylene of the formula $CH_2(OC_kH_{2k})_r$ where k is 2 and r is 1 to 20.

4. A compound according to claim 1 of the structure

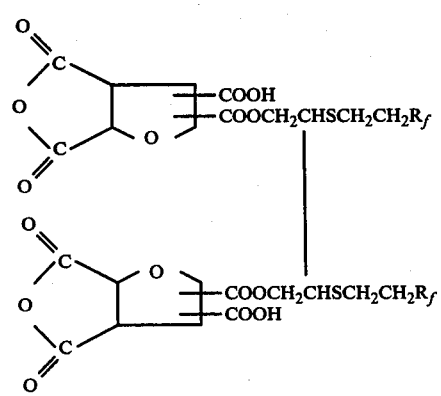

where $R_f$ is perfluoroalkyl of 6 to 18 carbon atoms.

5. A compound according to claim 1 of the structure
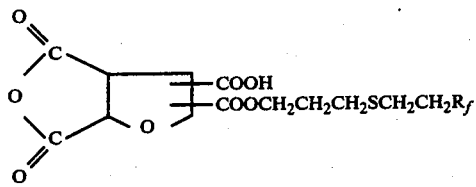
where $R_f$ is perfluoroalkyl of 6 to 18 carbon atoms.
6. A compound according to claim 1 of the structure
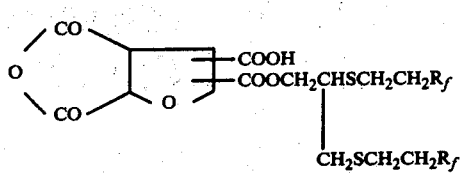
where $R_f$ is perfluoroalkyl of 6 to 18 carbon atoms.
7. A compound according to claim 1 of the structure
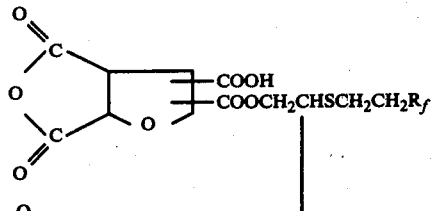
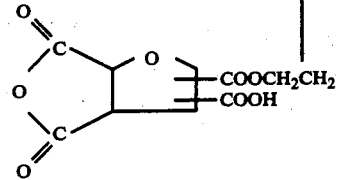
where $R_f$ is perfluoroalkyl of 6 to 18 carbon atoms.
* * * * *